(12) United States Patent
Bräuer (10) Patent No.: US 8,637,839 B2
(45) Date of Patent: Jan. 28, 2014

(54) METHOD FOR OPERATING A PARTICLE THERAPY SYSTEM

(75) Inventor: Martin Bräuer, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 225 days.

(21) Appl. No.: 13/081,433

(22) Filed: Apr. 6, 2011

(65) Prior Publication Data

US 2012/0119114 A1 May 17, 2012

(30) Foreign Application Priority Data

Apr. 7, 2010 (DE) .......................... 10 2010 014 002

(51) Int. Cl.
*G21K 5/00* (2006.01)
(52) U.S. Cl.
USPC ................... 250/492.3; 250/492.1; 250/492.2
(58) Field of Classification Search
USPC ...................................................... 250/492.3
See application file for complete search history.

(56) References Cited

U.S. PATENT DOCUMENTS

| | | | |
|---|---|---|---|
| 5,260,581 A | 11/1993 | Lesyna et al. | |
| 6,717,162 B1 * | 4/2004 | Jongen | 250/505.1 |
| 6,745,072 B1 | 6/2004 | Badura et al. | |
| 6,873,123 B2 * | 3/2005 | Marchand et al. | 315/502 |
| 7,928,415 B2 * | 4/2011 | Bert et al. | 250/492.3 |
| 8,129,699 B2 * | 3/2012 | Balakin | 250/492.3 |
| 2007/0114464 A1 * | 5/2007 | Birgy et al. | 250/494.1 |
| 2010/0060209 A1 | 3/2010 | Balakin | |

FOREIGN PATENT DOCUMENTS

| | | |
|---|---|---|
| DE | 199 07 138 A1 | 8/2000 |
| JP | 11329800 A | 11/1999 |
| WO | WO 03/069634 A2 | 8/2003 |
| WO | WO 03/092340 A1 | 11/2003 |
| WO | WO 2009/056165 A1 | 5/2009 |
| WO | WO 2010/149740 A1 | 12/2010 |

OTHER PUBLICATIONS

German Office Action dated Aug. 24, 2010 for corresponding German Patent Application No. DE 10 2010 014 002.3-54 with English translation.
Shinji Sato et al., Dynamic intensity control system with RF-knockout slow-extraction in the HIMAC synchrotron, Nuclear Instruments and Methods in Physics Research A. 574, pp. 226-231, 2007.
K. Noda et al., "Slow beam extraction by a transverse RF field with AM and FM," Nuclear Instruments and Methods in Physics Research A 374, pp. 269-277, 1996.
European Search Report and Written Opinion dated Aug. 19, 2011 for EP 11 15 6003.3-1269 with English translation.

* cited by examiner

*Primary Examiner* — Phillip A Johnston
(74) *Attorney, Agent, or Firm* — Lempia Summerfield Katz LLC (57) ABSTRACT

The present embodiments relate to a method for operating a particle therapy system. The particle therapy system includes a particle generation device, a beam generating device for generating a particle beam from at least one portion of the generated irradiation particles, a measuring device for automatically measuring a particle beam intensity of the particle beam, and a particle beam influencing device. The particle beam influencing device is configured to adjust the particle beam intensity as a function of the measured particle beam intensity and a predefined setpoint value for the particle beam intensity.

20 Claims, 4 Drawing Sheets

METHOD FOR OPERATING A PARTICLE THERAPY SYSTEM

This application claims the benefit of DE 10 2010 014 002.3, filed Apr. 7, 2010.

BACKGROUND

The present embodiments relate to a method for operating a particle therapy system and the particle therapy system.

Particle therapy systems are used for treating tumors using heavy particles such as, for example, protons or carbon ions. This includes irradiating a tumor with heavy particles using a raster scan method, for example. As well as tumors of patients, phantoms may also be irradiated (e.g., for research or maintenance purposes). The basis of the raster scan method is that the intensity of the radiation delivered by a particle generation and acceleration device is set for each ISO energy layer, and the dose applied to each raster scanning point is acquired in realtime and maintained for each scanning point until the planned target dose is reached. The radiation may be switched on and off with the aid of fast magnets, for example. Since a minimum time per scanning point is used while the radiation is applied to a scanning point, the minimum time, during which the radiation is applied to a scanning point at a minimum dose, determines the maximum beam intensity that may be used. The technological schemes for extracting the particle beam from the particle generator and accelerator device may lead to particle stream profiles that are subject to great fluctuations. Typical schemes for extracting the particle beams are, for example, resonance extraction or extraction using a knock-out exciter (e.g., KO exciter). The generated particle stream profiles are dominated by rapid fluctuations in the range of several microseconds and change (e.g., at the start of the extraction in addition to a time domain of several tens of milliseconds up to several seconds).

Figure 2:
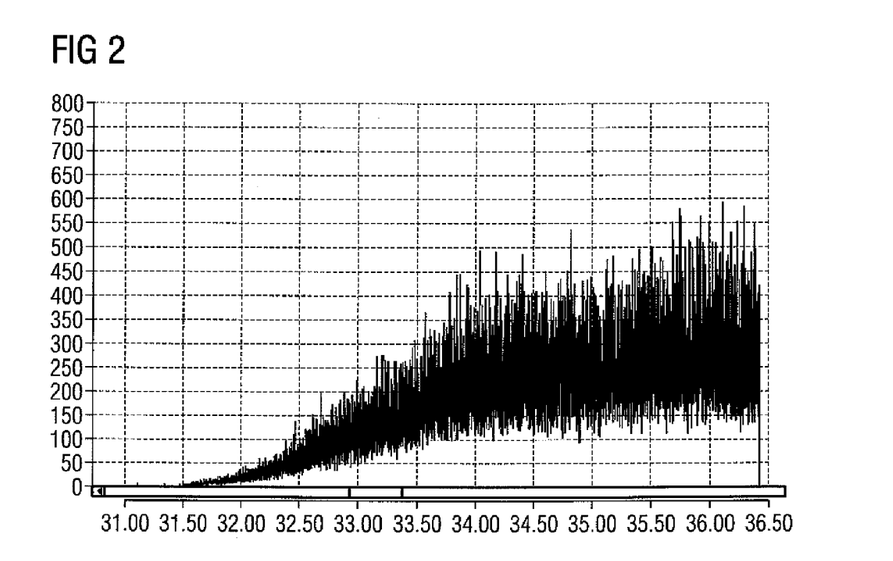
FIG. 2 shows a variation in intensity of a particle beam over time according to the prior art.

FIG. 2 shows a variation in intensity over time of a particle beam according to the prior art. The intensity was measured at a resolution of 50 µs. Both the long-term fluctuations and the very short-lived fluctuations are shown.

A method for emitting radiation of a charged particle beam and an acceleration device are known from JP-11329800. The acceleration device includes a device for impressing a high frequency, a deflecting device for an emission, a current measuring device and a calculating machine. The device for impressing the high frequency generates a high-frequency electric field, magnetic field or electromagnetic field on the basis of a high-frequency signal in order to impress the high-frequency field onto a charged particle stream. The deflecting device emits the charged particle beam that is moved outside of a resonance stability limit by the device for impressing the high frequency. The current measuring device measures a value of a current of the charged particle beam that is emitted by the deflecting device for an emission. The calculating machine determines an intensity of the high-frequency signal in accordance with the value of the current measured by the current measuring device.

Due to the strong fluctuations in particle beam intensity, which is evident in, for example, resonance extraction, radiation technology is currently implemented such that irradiation intensities exhibiting very high variability are accepted. Relatively long radiation exposure times are accepted that are dominated by the dose of scanning points having the lowest dose. In order to obtain acceptable radiation exposure times, the minimum doses per scanning point are set to a relatively high level at the planning stage. In this way, extreme cases, in which the duration of the beam application becomes very long due to the restriction to the small intensity, may be avoided. In certain situations, disproportionately high doses may be accepted at scanning points with a low dose requirement.

SUMMARY AND DESCRIPTION

Figure 1:
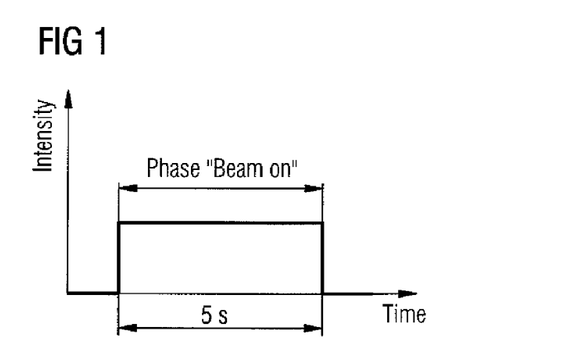
FIG. 1 shows a desired variation in intensity of a particle beam over time.

It would be desirable if a particle beam intensity (e.g., a number of projectiles or particles per time unit) runs in approximately the same shape as the rectangular function shown in FIG. 1. In other words, it would be desirable if the particle beam intensity rises very steeply to the desired intensity at a predetermined time instant and declines, again very steeply, after a predetermined time of, for example, 5 seconds.

The present embodiments may obviate one or more of the drawbacks or the limitations in the related art. For example, the operation of a particle therapy system may be improved such that radiation exposure times are shortened and both small and large radiation doses may be applied at different scanning points.

In one embodiment, a method for operating a particle therapy system is provided. The method includes generating and accelerating irradiation particles and generating a particle beam from at least one portion of the generated irradiation particles. A particle beam intensity of the particle beam is measured automatically. A plurality of scanning points is automatically irradiated sequentially with the particle beam in accordance with a predefined irradiation plan. In the irradiation plan, each scanning point of the plurality of scanning points is assigned a setpoint value for the particle beam intensity at the scanning point. The particle beam intensity is influenced automatically as a function of the measured particle beam intensity and the individually specified setpoint value for the particle beam intensity of the scanning point that is to be irradiated.

Because the particle beam intensity is measured and influenced or adjusted automatically in accordance with the predefined setpoint value, variations in radiation intensity as a function of the time may be realized. The variations in radiation intensity, for example, come very close to the desired waveform shown in FIG. 1, having a very steep rise, followed by a constant progression and a fast decline. Detectors used in particle therapy systems for measuring the dose applied per scanning point may be used, for example, for automatic sensing of the particle beam intensity. There is no need to introduce additional detectors that adversely affect the beam quality and consequently the result of the medical treatment into the particle beam. The beam intensity measured by the detectors may be passed on in digital form, for example, in realtime to a digital controller. Standard industrial bus signals may be used, for example, for transmitting the digitized measurement signals. The controller may be, for example, a PID controller that uses a proportional regulating function, an integrating regulating function and a differentiating regulating function. The PID controller may be suitable for correcting both the fast and the slow fluctuations shown in FIG. 2. Alternatively, other known controllers may also be used. An analog form of transmission may also be provided in addition to digital transmission of the particle beam intensity measured by the detectors.

The beam intensity is no longer limited by the scanning point having the lowest dose, and the radiation exposure time may be considerably reduced. The minimum doses per scanning point may be set to much lower levels in the irradiation plan. This enables an improved homogeneity, conformity of the irradiation to be achieved and the radiation exposure time to be reduced. This leads to a significant increase in patient throughput and consequently to a more effective use of the particle therapy system.

A change to the setpoint value during the sequential irradiation of the plurality of scanning points may be provided at certain scanning points. A change in the setpoint value may take place during the irradiation of the scanning points associated with an ISO energy layer. The beam intensity is no longer limited by the lowest-dose scanning point in the ISO energy layer, and the radiation exposure time may be considerably reduced. This gives greater flexibility in the irradiation planning, since the minimum doses per scanning point may be set to significantly lower values.

In one embodiment, the particle beam is directed to a particle beam output of a treatment station, and the particle beam intensity is measured at the particle beam output of the treatment station. This enables the automatic influencing of the particle beam intensity to be set such that the desired particle beam intensity is provided at the particle beam output of the treatment station. As a result, an influencing of the particle beam intensity may be taken into account when the particle beam is directed to the particle beam output.

According to another embodiment, the irradiation particles are generated and accelerated by a synchrotron and/or a linear accelerator. Alternatively, the irradiation particles may also be generated and accelerated by a cyclotron. When the synchrotron and the linear accelerator are used, a knock-out exciter may be used to decouple a fraction of the irradiation particles in order to influence the particle beam intensity. The knock-out exciter is controlled, for example, with the aid of a control unit and applies a radio frequency of adjustable strength to the particle beam in the accelerator. The higher the power, the more particles are decoupled per time unit. In order to obtain a desired variation in particle beam intensity, the output power is adjusted automatically in the control unit of the knock-out exciter, for example, using the PID controller. This eliminates the usual need to set parameters of functions that adjust the time characteristic of the output power of the knock-out exciter for a pilot control operation. The high constancy of the particle beam intensity over time makes the application of the particle beam more precise and more homogeneous. This also leads to simplification of control and monitoring systems for application of the particle beam, as a result of which operation becomes safer and more reliable. With the optimal and constant radiation intensity thus achieved, the frequency of beam interruptions (e.g., interlocks) may be reduced. As a result of the reduced frequency of the beam interruptions, the treatment may be carried out more quickly, and the particle therapy system may be used more efficiently.

In one embodiment, the particle beam may be directed to one treatment station of a plurality of treatment stations. The particle beam intensity (e.g., the applied particle beam intensity) is measured at each treatment station of the plurality of treatment stations, and the measured particle beam intensity of the treatment station, to which the particle beam is currently being directed, is automatically used for influencing the particle beam intensity. By measuring the particle beam intensity at each treatment station of the plurality of treatment stations and using the particle beam intensity to influence the particle beam intensity, the desired radiation intensity may be provided at the treatment station at which an irradiation session is currently being performed.

According to another embodiment, quality information relating to a particle generation device (e.g., the synchrotron, the linear accelerator or the cyclotron) is determined. The quality information is determined automatically as a function of the measured particle beam intensity and the current influencing of the particle beam intensity. For example, if the number of particles stored in the accelerator changes over time due to technical problems, then in the case of the synchrotron with the linear accelerator, the setting of the fraction of decoupled irradiation particles is correctively adjusted in order to maintain the predefined setpoint value for the particle beam intensity. By suitable logging and evaluation of the setting of the fraction of decoupled irradiation particles, the information relating to the quality of the particle generation device may be derived. Measures for preventive maintenance of the particle generation device may be derived on the basis of the quality information, for example.

According to yet another embodiment, a particle therapy system is provided. The particle therapy system includes a particle generation device for generating and accelerating irradiation particles, a beam generating device, a measuring device, a raster scan controller and a particle beam influencing device. The beam generating device (e.g., a knock-out exciter) is configured such that the beam generating device generates a particle beam from at least one portion of the irradiation particles of the particle generation device. The measuring device is operable to measure a particle beam intensity of the particle beam automatically. The particle beam influencing device is configured such that the particle beam influencing device influences and consequently adjusts the particle beam intensity as a function of the measured particle beam intensity and a predefined setpoint value for the particle beam intensity. The raster scan controller is configured for irradiating a plurality of scanning points sequentially with the particle beam in accordance with a predefined irradiation plan. The irradiation plan assigns a setpoint value for the particle beam intensity to each scanning point of the plurality of scanning points. The raster scan controller is coupled to the particle beam influencing device and transmits the setpoint value of a scanning point that is to be irradiated to the particle beam influencing device. The particle beam influencing device uses the setpoint value to adjust the desired particle beam intensity for the scanning point that is to be irradiated. Both small and large irradiation doses may be implemented for different scanning points and provided in short radiation exposure times. As a result, the use of the particle therapy system may be improved and the treatment time for the patient shortened.

The particle therapy system may also include a particle beam feeder unit that directs the particle beam to a particle beam output of a treatment station. In one embodiment, the measuring device may be disposed at the particle beam output to automatically measure the particle beam intensity. Using the measuring device, a precise and desired beam intensity may be provided at the particle beam output.

The particle therapy system may include a particle beam feeder unit that may direct the particle beam to one treatment station of a plurality of treatment stations. A measuring device for automatically measuring the particle beam intensity of the emitted particle beam (e.g., for detecting the applied particle beam intensity) is provided at each treatment station of the plurality of treatment stations. The particle therapy system may also include a switchover unit that directs the measured particle beam intensity of the one treatment station, to which the particle beam is currently being directed to the particle beam influencing device. This enables the plurality of treatment stations to be supplied with the particle beam, as a result of which the particle therapy system may be used more efficiently. With the aid of the switchover unit, the desired particle beam intensity is provided at each treatment station of the plurality of treatment stations.

According to another embodiment, the particle therapy system includes a quality determining device for determining information relating to the quality of the particle generation device. The quality information is determined by the quality determining device as a function of the measured particle beam intensity and the influencing of the particle beam intensity by the particle beam influencing device. This enables malfunctions to be detected and rectified at an early stage or assists in the scheduling of maintenance activities on the particle therapy system in the future.

The above-described particle therapy system is suitable for performing the above-described method and therefore includes the advantages described in connection with the method.

The present embodiments include a computer program product (e.g., software that may be loaded into a memory (e.g., a non-transitory memory) of a programmable controller) of the particle beam influencing device, for example, of the particle therapy system. All of the above-described embodiments of the method may be implemented using instructions of the computer program product when the computer program product is executed in the particle therapy system.

The present embodiments provide an electronically readable data medium (e.g., a CD or DVD), on which electronically readable control information (e.g., software) is stored. When the control information is read from the data medium and stored in a control device (e.g., the particle beam influencing device of the particle therapy system), the embodiments of the above-described method may be performed with the particle therapy system.

The present embodiments are explained below with reference to the drawings.

The foregoing and following description of the individual features, their advantages and their effects relate both to the device and to the method, without this being explicitly mentioned in detail in each case. The individual features disclosed in the method may also be used in combinations other than those shown.

DETAILED DESCRIPTION OF THE DRAWINGS

Figure 3:
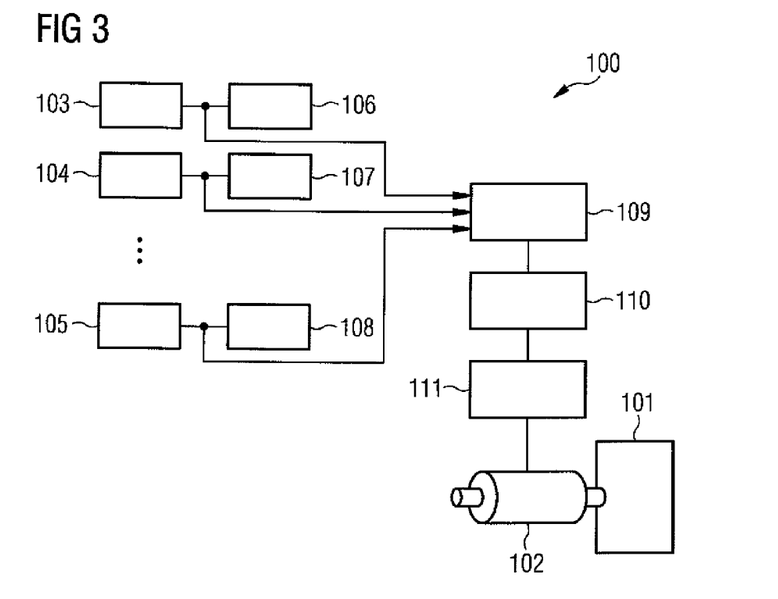
FIG. 3 shows a schematic representation of one embodiment of a particle therapy system.

FIG. 3 shows a particle therapy system 100. The particle therapy system 100 includes a particle generation device 101, a beam generating device 102 and a particle beam feeder unit (not shown). Irradiation particles, protons or carbon ions, for example, are generated and accelerated in the particle generation device 101 (e.g., a linear accelerator and a synchrotron or a cyclotron). In the case of the synchrotron and the linear accelerator, a fraction of the generated and accelerated particles is decoupled from the particle generation device 101 with the aid of the beam generating device 102 and directed as a particle beam into the particle beam feeder unit (not shown). The beam generating device 102 may be, for example, a knock-out exciter that applies a radio frequency of adjustable power to the particle beam in the particle generation device 101. The higher the power, the more particles are decoupled per time unit and supplied to the decoupled particle beam. The particle beam feeder unit directs the generated particle beam to one treatment station of a plurality of treatment stations that may be arranged, for example, in different treatment rooms. The particle therapy system also includes a measuring device 103-105 at each treatment station for the plurality of treatment stations for the purpose of measuring a particle beam intensity of the particle beam that is supplied to the one treatment station by the particle beam feeder unit. Three treatment stations are shown by way of example in FIG. 3, the measuring device 103 being disposed at a first treatment station, the measuring device 104 being disposed at a second treatment station, and the measuring device 105 being disposed at a third treatment station. The measuring devices 103-105 measure the beam intensity, for example, with the aid of gas-filled ionization chambers and parallel-plate capacitors arranged in the gas-filled ionization chambers. The acquired particle beam intensity indicates a particle beam dose per time unit. Each measuring device 103-105 is assigned a dose determining device 106-108 that integrates the particle beam intensities of the assigned measuring devices over time in order to determine a particle beam dose at the treatment station.

The particle therapy system 100 also includes a switchover unit 109 that is coupled to the measuring devices 103-105. The switchover unit 109 is also coupled to a particle beam influencing device 110. The particle beam influencing device 110 may include, for example, an electronic controller such as a microprocessor. A higher-order controller (not shown) of the particle therapy system 100 that also controls the particle beam feeder unit provides the switchover unit 109 with information indicating which treatment station is currently being supplied with the particle beam by the particle beam feeder unit. The switchover unit 109 selects the measured particle beam intensity of one of the measuring devices 103-105 in order to pass the measured particle beam intensity on to the particle beam influencing device 110. The connection between the measuring devices 100-105 and the switchover unit 109 may transmit, for example, digital signals over separate lines or via a bus system. The higher-order controller provides the particle beam influencing device 110 with a setpoint value (e.g., a predefined setpoint value) for the particle beam intensity, and the particle beam influencing device 110 provides a control value for a drive circuit 111 for the beam generating device 102. The control value for the drive circuit 111 is determined by the particle beam influencing device 110 as a function of the measured particle beam intensity by one of the measuring devices 103-105 and the predefined setpoint value for the particle beam intensity. For this purpose, the particle beam influencing device 110 includes a PID controller, for example. The PID controller provides the control value for the drive circuit 111, using which the radio frequency power of the knock-out exciter is set, for example, in order to regulate the decoupling rate or extraction rate of the particles in the synchrotron to a temporally constant rate that is predefined by the setpoint value. The particle beam influencing device 110 may be implemented, for example, in the form of a standard industrial controller (e.g., a programmable logic controller) and be integrated as a standard module into the particle therapy system. The control value that is transmitted by the particle beam influencing device 110 to the drive circuit 111 of the beam generating device 102 may be transmitted, for example, in analog or digital form.

Alternatively, the switchover unit 109, acting independently of the higher-order controller, may also pass on the measured particle beam intensity from the one measuring device 103-105 to the particle beam influencing device 110. The particle beam influencing device 110 is disposed at a treatment station that reports a reference or setpoint intensity different from zero, since for reasons of patient safety, a higher-order system provides in any case that only one treatment station is supplied with a particle beam at any given time.

The particle therapy system 100 may also include a quality determining device (not shown) that is integrated, for example, in the higher-order control device of the particle therapy system 100. The quality determining device records the control value that is output by the particle beam influencing device 110 to the drive circuit 111 and logs the control values over the course of time together with the setpoint values for the particle beam intensity. If, for example, the number of particles generated and stored by the particle generation device 101 changes over time due, for example, to technical problems, the control value of the particle beam influencing device 110 will assume anomalous values (e.g., upper or lower limit values) before an end of the planned radiation exposure time is reached. Using suitable logging and evaluation of the time instant at which the limit value is reached, a quality parameter may be derived for the operation of the particle generation device 101. Measures for preventive maintenance of the particle generation device 101 may be derived on the basis of the quality parameter.

If the control value that is output by the particle beam influencing device 110 to the drive circuit 111 reaches a limit value, the control value may also signal that there are no more particles in the accelerator of the particle generation device 101. This information may be used in order to perform the regulated application of the particle beam until such time as the drive circuit 111 signaled that there are no more particles in the accelerator by the control value from the particle beam influencing device 110. The number of particles stored in the accelerator may be used to optimum effect. This may contribute toward reducing the load on the environment, since otherwise, the stored and accelerated residual beam would be annihilated, resulting in radioactive contamination of an annihilation unit and/or parts of the system.

Figure 4:
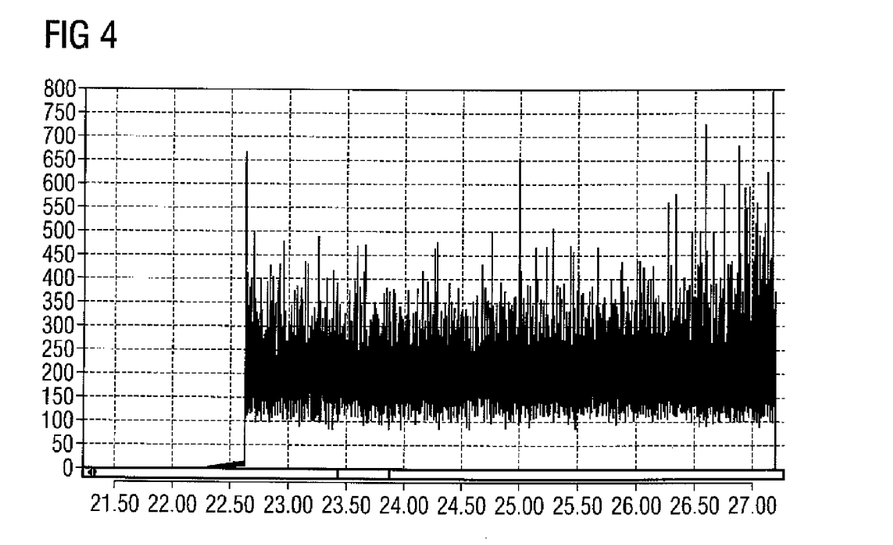
FIG. 4 shows a variation in intensity of a particle beam over time according to one embodiment.

Since the information relating to the particle beam intensity is output by the measuring devices or detectors 103-105 in realtime to the particle beam influencing device 110 for the purpose of regulating the particle beam intensity, a more precise particle beam intensity may be provided at the treatment stations. FIG. 4 shows the variation over time of the particle beam intensity regulated according to the present embodiments. As in FIG. 2, the particle beam intensity was measured at intervals of 50 µs. The regulation function was activated at time instant t=22.7 s. Compared with FIG. 2, FIG. 4 shows that the long-term fluctuations have been successfully reduced to a significant degree as a result of the regulation function.

Figure 5:
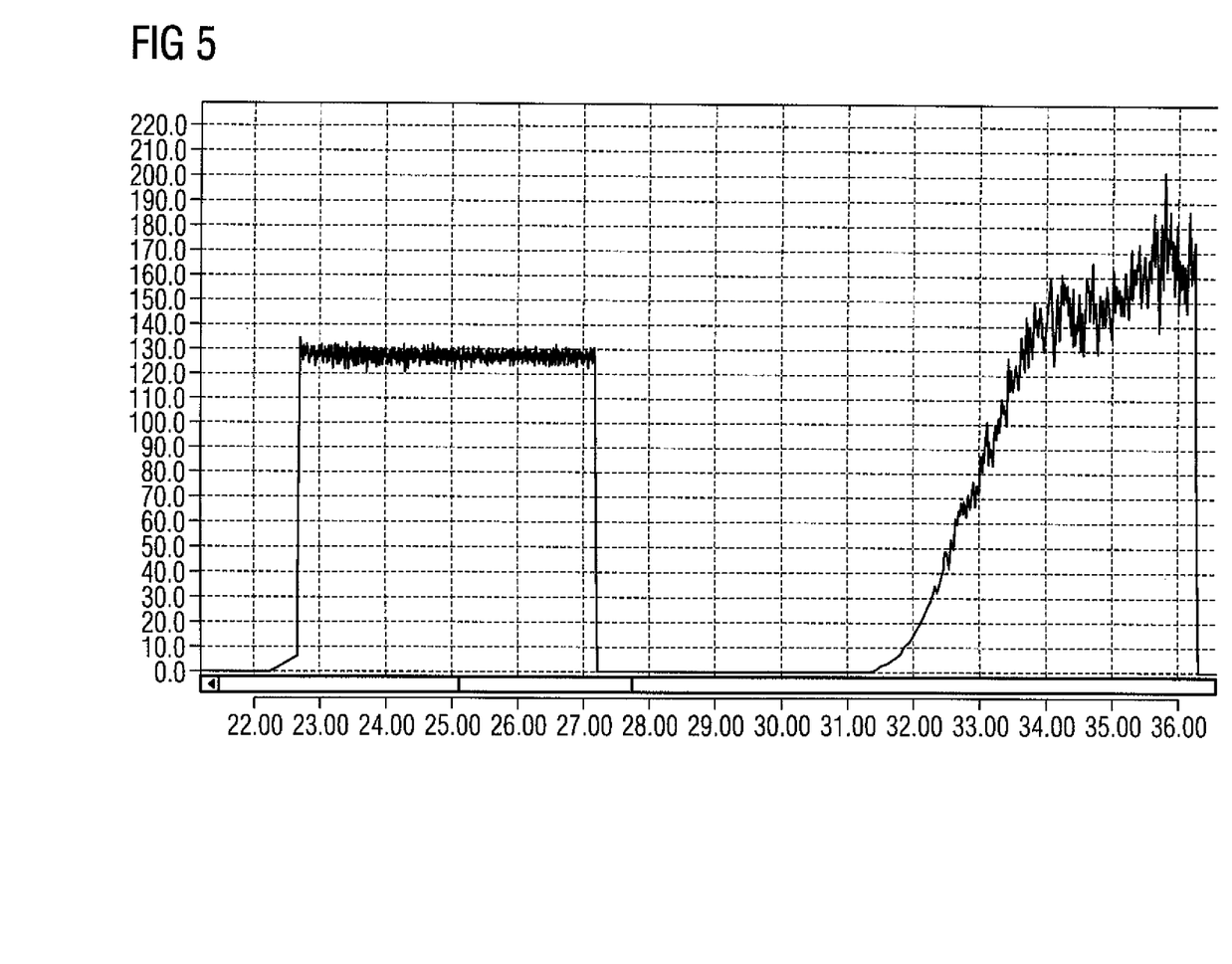
FIG. 5 shows the variation in intensity of the particle beam over time according to one embodiment in comparison with the variation in intensity of the particle beam over time according to the prior art.

FIG. 5 shows a comparison of the particle beam intensity with and without regulation function. In FIG. 5, the intensity data has been smoothed using an FIR filter by averaging over 20 ms. As can be seen from FIG. 5, not just the slow fluctuations, but also the short-lived fluctuations have been significantly reduced in the regulated particle beam in the time range from approximately 22.7 s to 27.2 s. In the unregulated intensity curve from approximately 31.4 s to 36.3 s, the significantly stronger short-term fluctuations may also be seen in addition to the considerably stronger slow fluctuations.

In a particle beam therapy session, tumors may be treated using a raster scan method. In the raster scan method, the tumor is subdivided logically into a plurality of raster scanning volumes (e.g., scanning points), and an irradiation dose is assigned to each of the scanning points in an irradiation plan. In order to irradiate a scanning point, the particle beam is directed onto the scanning point, and particles having a predetermined energy that determines the penetration depth of the particles are delivered into the tumor. The treatment plan may have widely varying particle doses for each of the scanning points.

Figure 6:
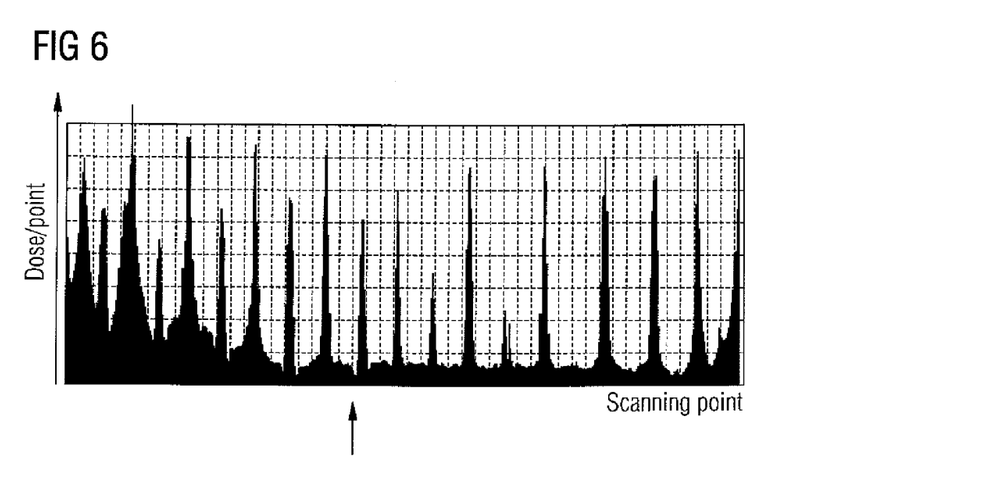
FIG. 6 shows an irradiation plan that assigns an irradiation dose to each scanning point of the irradiation plan.

FIG. 6 shows by way of example desired particle doses for a plurality of scanning points of an irradiation plan. In one embodiment, a minimum time per scanning point is used during the time the irradiation is applied onto the scanning point. The minimum time for the irradiation of the scanning point with a minimum dose limits the maximum beam intensity that may be used. In FIG. 6, a scanning point having a minimum dose is identified by an arrow. In a particle therapy system according to the prior art, in which the particle beam intensity is not controlled as described hereintofore, a relatively long radiation exposure time is accepted for many scanning points with a significantly higher dose, the radiation exposure time being dominated by the dose of the scanning point having the lowest dose.

In the particle therapy system 100 shown in FIG. 3, which has a regulated particle beam intensity, the particle beam intensity may be varied dynamically from scanning point to scanning point. For example, the setpoint value for the beam intensity may be derived automatically from the irradiation plan and transmitted in a synchronized manner to the particle beam influencing device 110 in realtime during the irradiation of the different scanning points. Since the accelerator system may have the characteristic of responding to a control variable modification of the controller with a delay time of several milliseconds, the specification of the setpoint value for the particle beam influencing device 110 may be output with a "lead time." If a chronologically sorted list containing the data of the scanning points (irradiation plan) is present in the higher-order control system prior to the start of the irradiation, the optimal time instant for passing the setpoint value to the particle beam influencing device 110 may be determined in a preprocessing stage using a suitable algorithm. The beam intensity may be optimally adapted to the requirements of the respective scanning point at all times.

Figure 7:
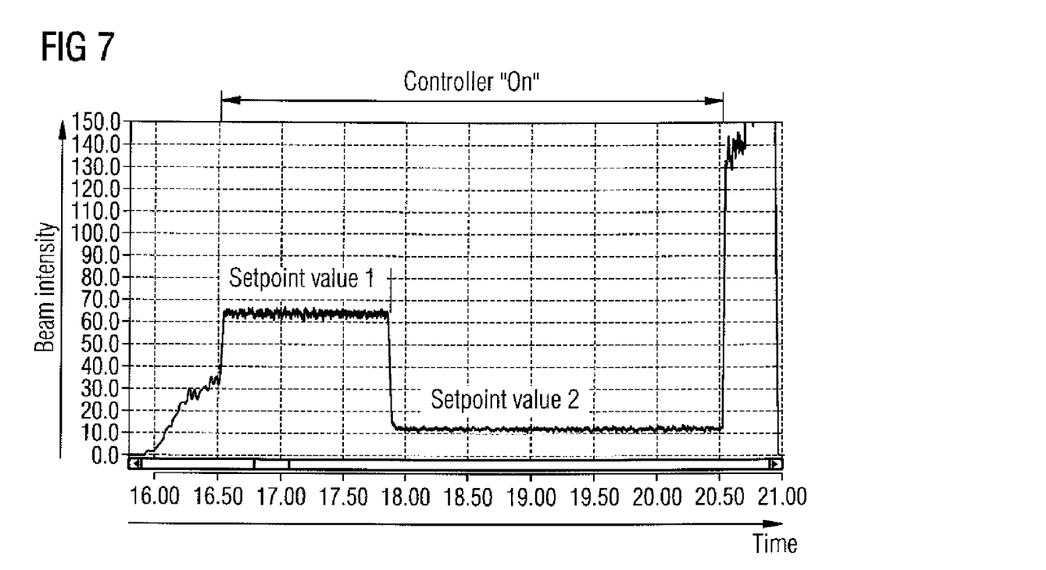
FIG. 7 shows a variation in intensity of a particle beam over time according to another embodiment.

FIG. 7 shows a change in the radiation intensity as a result of a change to a predefined setpoint value.

An advantage of the present embodiments derives from the fact that the beam intensity is no longer limited by the scanning point having the lowest dose. By varying the particle beam intensity, scanning points, for which a high beam dose is provided with the designated dose in a considerably shorter time, may be irradiated. The total radiation exposure time may be considerably reduced. The minimum doses per scanning point may be set to a much lower level in the therapy planning systems. An improvement in the homogeneity and conformity of the irradiation is thus achieved. A long radiation exposure time is avoided owing to the active regulation of the particle stream intensity. Thus, the patient throughput of the particle therapy system is significantly increased and the quality of the treatment plans improved.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a particle therapy system, the method comprising:
generating and accelerating irradiation particles;
generating a particle beam from at least a portion of the generated irradiation particles;
automatically measuring a particle beam intensity of the particle beam;
automatically sequentially irradiating a plurality of scanning points with the particle beam in accordance with a predefined irradiation plan, wherein the irradiation plan assigns an irradiation dose to each scanning point of the plurality of scanning points, and wherein a set-point value for the particle beam intensity is assigned to each scanning point of the plurality of scanning points based on the irradiation dose assigned to the scanning point by the predefined irradiation plan; and
automatically influencing the particle beam intensity as a function of the measured particle beam intensity and the setpoint value of the scanning point that is to be irradiated.

2. The method as claimed in claim 1, further comprising directing the particle beam to a particle beam output of a treatment station,
wherein the particle beam intensity is measured at the particle beam output.

3. The method as claimed in claim 1, wherein generating the particle beam comprises decoupling a fraction of the generated irradiation particles with the aid of a knock-out exciter, influencing the particle beam intensity with a radio frequency power of the knock-out exciter being set automatically.

4. The method as claimed in claim 1, wherein the setpoint value of the particle beam intensity has a non-constant variation over time.

5. The method as claimed in claim 1, wherein a proportional regulating function, an integrating regulating function, or a differentiating regulating function is used to influence the particle beam intensity.

6. The method as claimed in claim 1, wherein generating and accelerating the irradiation particles comprises using a linear accelerator and a synchrotron or a cyclotron.

7. The method as claimed in claim 1, further comprising directing the particle beam to one treatment station of a plurality of treatment stations, the particle beam intensity being measured at each treatment station of the plurality of treatment stations,
wherein the measured particle beam intensity of the one treatment station is automatically used for influencing the particle beam intensity.

8. The method as claimed in claim 1, further comprising determining information relating to quality of a particle generation device that generates and accelerates the irradiation particles,
wherein the information is determined automatically as a function of the measured particle beam intensity and the setting of the fraction of the decoupled irradiation particles.

9. A particle therapy system comprising:
a particle generation device operable to generate and accelerate irradiation particles;
a beam generating device operable to generate a particle beam from at least a portion of the generated irradiation particles;
a measuring device operable to automatically measure a particle beam intensity of the particle beam;
a raster scan controller configured to sequentially irradiate scanning points with the particle beam in accordance with a predefined irradiation plan, wherein the irradiation plan assigns an irradiation dose to each of the scanning points, and wherein a set-point value for the particle beam intensity is assigned to each of the scanning points based on the irradiation dose assigned to the scanning point by the predefined irradiation plan; and
a particle beam influencing device that is coupled to the raster scan controller and is configured to alter the particle beam intensity as a function of the measured particle beam intensity and the assigned setpoint value for the particle beam intensity of the scanning point that is to be irradiated.

10. The particle therapy system as claimed in claim 9, further comprising a particle beam feeder unit operable to direct the particle beam to a particle beam output of a treatment station,
wherein the measuring device is disposed at the particle beam output.

11. The particle therapy system as claimed in claim 9, wherein the beam generating device comprises a knock-out exciter having a control input operable to adjust a radio frequency power, the knock-out exciter being operable to vary a decoupled fraction of the irradiation particles, and
wherein the particle beam influencing device sets the control input of the knock-out exciter as a function of the measured particle beam intensity and the predefined setpoint value for the particle beam intensity in order to alter the particle beam intensity.

12. The particle therapy system as claimed in claim 9, wherein the setpoint value for the particle beam intensity has a non-constant variation over time.

13. The particle therapy system as claimed in claim 9, wherein the particle beam influencing device comprises a proportional controller, an integrating controller, or a differentiating controller.

14. The particle therapy system as claimed in claim 9, wherein the particle generation device comprises a linear accelerator and a synchrotron or a cyclotron.

15. The particle therapy system as claimed in claim 9, further comprising:
a particle beam feeder unit operable to direct the particle beam to one treatment station of a plurality of treatment stations, wherein a measuring device operable to automatically measure the particle beam intensity of the output particle beam is provided at each treatment station of the plurality of treatment stations; and
a switchover unit configured to direct the measured particle beam intensity of the one treatment room to the particle beam influencing device.

16. The particle therapy system as claimed in claim 9, further comprising a quality determining device operable to determine information relating to quality of the particle generation device as a function of the measured particle beam intensity and the influencing of the particle beam intensity.

17. The particle therapy system as claimed in claim 9, wherein the particle therapy system is configured for:
generating and accelerating the irradiation particles;
generating the particle beam from at least the portion of the generated irradiation particles; automatically measuring the particle beam intensity of the particle beam;

automatically sequentially irradiating the scanning points with the particle beam in accordance with the predefined irradiation plan; and automatically influencing the particle beam intensity as a function of the measured particle beam intensity and the setpoint value of the scanning point that is to be irradiated.

18. A non-transitory computer readable medium comprising a computer program product that, when executed by a particle beam influencing device of a particle therapy system, causes the particle beam influencing device to perform a method for operating the particle therapy system, the method comprising:

generating and accelerating irradiation particles;

generating a particle beam from at least a portion of the generated irradiation particles;

automatically measuring a particle beam intensity of the particle beam;

automatically sequentially irradiating a plurality of scanning points with the particle beam in accordance with a predefined irradiation plan, wherein the irradiation plan assigns an irradiation dose to each scanning point of the plurality of scanning points, and wherein a set-point value for the particle beam intensity is assigned to each scanning point of the plurality of scanning points based on the irradiation dose assigned to the scanning point by the predefined irradiation plan; and automatically influencing the particle beam intensity as a function of the measured particle beam intensity and the setpoint value of the scanning point that is to be irradiated.

19. A non-transitory electronically readable data medium on which is stored electronically readable control information that is configured such that the electronically readable control information performs a method for operating a particle therapy system when the electronically readable data medium is used in a particle beam influencing device, the method comprising:

generating and accelerating irradiation particles;

generating a particle beam from at least a portion of the generated irradiation particles; automatically measuring a particle beam intensity of the particle beam;

automatically sequentially irradiating a plurality of scanning points with the particle beam in accordance with a predefined irradiation plan, wherein the irradiation plan assigns an irradiation dose to each scanning point of the plurality of scanning points, and wherein a set-point value for the particle beam intensity is assigned to each scanning point of the plurality of scanning points based on the irradiation dose assigned to the scanning point by the predefined irradiation plan; and automatically influencing the particle beam intensity as a function of the measured particle beam intensity and the setpoint value of the scanning point that is to be irradiated.

20. The method as claimed in claim 3, wherein the setpoint value of the particle beam intensity has a non-constant variation over time.

* * * * *